(12) United States Patent
Lee et al.

(10) Patent No.: US 11,597,834 B2
(45) Date of Patent: Mar. 7, 2023

(54) BIODEGRADABLE POLYMER MICROPARTICLE FOR FILLER, MANUFACTURING METHOD THEREOF, FREEZE-DRIED BODY INCLUDING THE SAME, AND FILLER INJECTION INCLUDING THE SAME

(71) Applicant: ULTRA V CO., LTD., Incheon (KR)

(72) Inventors: Cheong Cheon Lee, Seoul (KR); Lia Priscilla, Seoul (KR); Min Seok Kwak, Seoul (KR); Jung Woo Han, Seoul (KR); Jung Ryul Ham, Paju-si (KR); Han Jin Kwon, Seoul (KR)

(73) Assignee: ULTRA V CO., LTD., Incheon (KR)

( * ) Notice: Subject to any disclaimer, the term of this patent is extended or adjusted under 35 U.S.C. 154(b) by 0 days.

(21) Appl. No.: 17/581,322

(22) Filed: Jan. 21, 2022

(65) Prior Publication Data
US 2022/0235221 A1 Jul. 28, 2022

(30) Foreign Application Priority Data

Jan. 22, 2021 (KR) .................. 10-2021-0009522

(51) Int. Cl.
| | | |
|---|---|---|
| C08L 67/02 | (2006.01) | |
| A61K 8/02 | (2006.01) | |
| A61L 27/26 | (2006.01) | |
| C08J 3/09 | (2006.01) | |
| C08L 1/02 | (2006.01) | |

(52) U.S. Cl.
CPC .......... *C08L 67/025* (2013.01); *A61K 8/0245* (2013.01); *A61L 27/26* (2013.01); *C08J 3/092* (2013.01); *C08J 3/093* (2013.01); *C08L 1/02* (2013.01); *A61K 2800/412* (2013.01); *A61K 2800/60* (2013.01); *C08L 2201/06* (2013.01); *C08L 2207/53* (2013.01)

(58) Field of Classification Search
None
See application file for complete search history.

(56) References Cited

U.S. PATENT DOCUMENTS

| | | | | |
|---|---|---|---|---|
| 2014/0228477 | A1* | 8/2014 | Jhaveri | C08F 8/42 524/824 |
| 2014/0332773 | A1* | 11/2014 | Chien | G02B 5/0242 524/561 |
| 2017/0129993 | A1* | 5/2017 | Choi | C08L 71/02 |
| 2018/0043061 | A1* | 2/2018 | Lee | A61L 31/146 |

FOREIGN PATENT DOCUMENTS

| | | |
|---|---|---|
| JP | 2020-521805 A | 7/2020 |
| KR | 10-2017-0111925 A | 10/2017 |
| KR | 10-2089560 B1 | 3/2020 |
| KR | 10-2173939 B1 | 11/2020 |

OTHER PUBLICATIONS

Zou et al. "Synthetic strategies for raspberry-like polymer composite particles," Polymer Chemistry 11:3370-3392, 2020 (Year: 2020).*
Li et al. "Core-corona polymer composite particles by self-assembled heterocoagulation based on a hydrogen-bonding interaction," Langmuir 22:8127-8133, 2006 (Year: 2006).*
Wagner et al. "Towards nanoscale composite particles of dual complexity," Journal of Colloid and Interface Science 355:115-123, 2011 (Year: 2011).*
"Decision to Grant a Patent" Office Action issued in KR 10-2021-0009522; mailed by the Korean Intellectual Property Office dated Mar. 30, 2021.
Hua Zou et al. "Synthetic Strategies for Raspberry-Like Polymer Composite Particles" Polym. Chem, 2020, pp. 3370-3392, vol. 11.
Rui Li et al. "Core-Corona Polymer Composite Particles by Self-Assembled Heterocoagulation Based on a Hydrogen-Bonding Interaction" Langmuir, Aug. 16, 2006, pp. 8127-8133, vol. 22, No. 19.
Communication pursuant to Article 94(3) EPC issued by the European Patent Office dated Dec. 9, 2022, which corresponds to European Patent Application No. 22152388.9-1102 and is related to U.S. Appl. No. 17/581,322.
Karl-Friedrich Arndt et al., "4 Molmasse und Molmassenbestimmung", Polymercharakterisierung, Jan. 1, 1996, pp. 92-107, Carl Hanser Verlag, ISBN: 978-3-146-17588-4.

* cited by examiner

*Primary Examiner* — Ileana Popa
*Assistant Examiner* — Alissa Prosser
(74) *Attorney, Agent, or Firm* — Studebaker & Brackett PC

(57) ABSTRACT

Disclosed herein are a biodegradable polymer microparticle for a filler comprising a core and a shell, wherein the core contains secondary particles including aggregates of a plurality of primary particles, the shell has a raspberry shaped structure, an average particle diameter ($D_{50}$) of the biodegradable polymer microparticle ranges from 20 to 200 μm, a manufacturing method thereof, a freeze-dried body including the same, and filler injection including the same.

11 Claims, 6 Drawing Sheets

BIODEGRADABLE POLYMER MICROPARTICLE FOR FILLER, MANUFACTURING METHOD THEREOF, FREEZE-DRIED BODY INCLUDING THE SAME, AND FILLER INJECTION INCLUDING THE SAME

CROSS-REFERENCE TO RELATED APPLICATIONS

The present application claims the benefit of priority to Korean Patent Application No. 10-2021-0009522, filed on Jan. 22, 2021, in the Korean Intellectual Property Office. The disclosure of the above-listed application is hereby incorporated by reference herein in its entirety.

BACKGROUND

1. Technical Field

The present disclosure relates to a biodegradable polymer microparticle for a filler, a manufacturing method thereof, a freeze-dried body including the same, and filler injection including the same.

2. Description of Related Art

Biodegradable polymer microparticles are materials that recently begin to get spotlight as a material for tissue repair applicable to the face and the whole body. The biodegradable polymer does not contain components harmful to the human body unlike conventional hyaluronic acid hydrogel, and can be decomposed over a long time of 6 months to 4 years, thereby being applicable to various purposes.

The biodegradable polymer microparticles used for a dermal filler is decomposed during several months to several years after being injected into the human body so as to completely dissipate, thereby providing wrinkle improvement effect through tissue repair during a corresponding period.

The biodegradable polymer microparticles are materials that do not exist in the human body, thereby causing a Foreign body reaction after injected into the body and stimulating self-collagen generation in the process. The foreign body reaction mechanism is not yet known exactly. However, according to the common contents suggested through a great deal of studies, the self-collagen generation is stimulated through adsorption of macrophages, formation of multi-nucleated giant cells, and collagenous encapsulation. Accordingly, the dermal fillers for the biodegradable polymer microparticles are effective for raising collagen density of the dermis reduced due to aging.

However, most of the biodegradable polymer microparticles are not hydrophilic and are disadvantageous for adsorption of macrophages since the surface of the microparticles is smooth. Therefore, the progress gets slower in the cell adsorption operation, thereby lengthening the action mechanism causing the self-collagen generation stimulation.

In order to solve the problem, methods for improving cell adsorption through a physical transformation of biodegradable polymer microparticles for a dermal filler have been proposed. The most efficient method among the methods is a method of increasing the surface area, which is a method capable of increasing the efficiency of self-collagen generation stimulation while providing an environment in which wider areas can be in contact with cells.

However, if the surface area is widened in a state of having an edge (acute angle) without any curved surface, since the biodegradable polymer microparticles may cause side effects by piercing tissues in the body, the surface areas of the microparticles for a dermal filler must be widened in a state of having a curved surface since where the surface has a curved surface.

For example, Korean Patent Laid-Open Publication No. 10-2017-0111925 discloses a micro capsule in the form of a raspberry, and proposes a method for manufacturing fine droplets by forming a multi-layer emulsion. That is, the conventional method is a method for manufacturing droplets not in a solid state but in a liquid state, thereby increasing density of ink in the field of a display film.

SUMMARY

The present disclosure has been made to solve the above-mentioned problems occurring in the prior art, and in an aspect of the present disclosure, it is an object to provide a biodegradable polymer microparticle for a filler to improve cell adsorption ability by increasing a surface area.

In another aspect of the present disclosure, it is another object to provide a method for manufacturing a biodegradable polymer microparticle for a filler.

In a further aspect of the present disclosure, it is a further object to provide a freeze-dried body for a filler.

In a still further aspect of the present disclosure, it is a further object to provide filler injection.

To accomplish the above objects, in an aspect of the present disclosure, there is provided a biodegradable polymer microparticle for a filler comprising a core and a shell, wherein the core contains secondary particles including aggregates of a plurality of primary particles, the shell has a raspberry shaped structure, an average particle diameter ($D_{50}$) of the secondary particle ranges from 20 to 200 μm.

In another aspect of the present disclosure, there is provided a freeze-dried body for a filler comprising: a biodegradable polymer microparticle according to any one among claims 1 to 4; and a biocompatible carrier.

In a further aspect of the present disclosure, there is provided injection for a filler comprising: a biodegradable polymer microparticle according to any one among claims 1 to 4; and one or more selected from injection water, sterilized water, and distilled water.

The injection for a filler further comprises a biocompatible carrier, wherein a mixing weight ratio of the biodegradable polymer microparticles and the biocompatible polymer microparticles is 80:20 to 20:80.

In a still further aspect of the present disclosure, there is provided a method for manufacturing biodegradable polymer microparticles for a filler according to any one among claims 1 to 4, the method comprising: a first operation of mixing a first composition containing organic solvent miscible with water and biodegradable polymers and a second composition containing first surfactant and water, and preparing a third composition containing biodegradable polymer microparticle precursors for a filler and stirring them; a second operation of adding and mixing a fourth composition containing the first composition containing the biodegradable polymers, second surfactant, and water to the first operation product, and stirring them to prepare a fifth composition containing biodegradable polymer microparticles; and a third operation of separating the biodegradable polymer microparticles from the fifth composition. In the second operation, the feed rate of the fourth composition is faster than the feed rate of the second composition of the first operation. The total content of the first surfactant and the second surfactant is 30 to 50 parts by weight with respect to 100 parts by weight of the total content of the biodegradable polymer microparticles. The stirring speed of the second operation is slower than the stirring speed of the first operation. In the second operation, the content of the second surfactant is more than the content of the first surfactant in the first operation. The content of the first surfactant in the first operation is 5 to 20 parts by weight with respect to 100 parts by weight of the total content of the biodegradable polymer microparticles, and the content of the second surfactant in the second operation is 25 to 30 parts by weight with respect to 100 parts by weight of the total content of the biodegradable polymer microparticles.

According to one aspect, provided are a biodegradable polymer microparticle for a filler, a manufacturing method thereof, a freeze-dried body including the same, and filler injection including the same. By using the biodegradable polymer microparticles, improved cell adsorption capacity can be provided. Additionally, when the biodegradable polymer microparticles are used as a dermal filler, it can increase an effect of self-collagen generation stimulation.

DETAILED DESCRIPTION

Figure 1A:
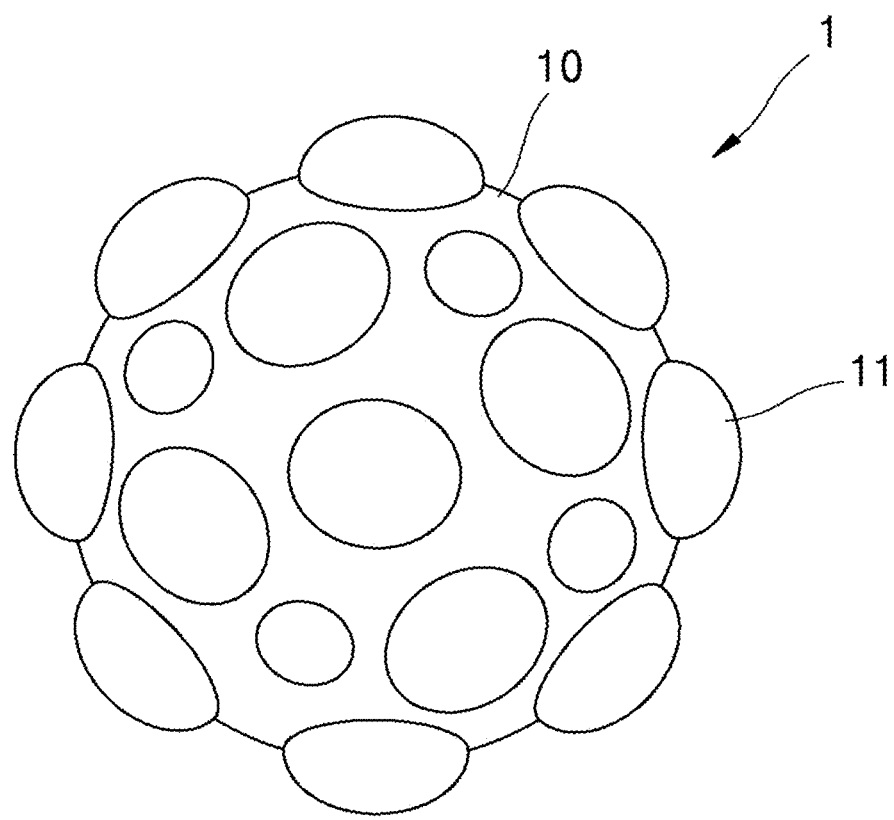
FIG. 1A is a schematic view illustrating a structure of a biodegradable polymer microparticle for a filler of the present disclosure.

The present inventive concept described below can apply various transforms and may have various embodiments, and will be described in detail with reference to the drawings. However, this is not intended to limit the inventive concept to particular embodiments, and it is to be understood that all of changes, equivalents, or substitutes are included in the technical scope of the present inventive concept.

Additionally, in the attached drawings, dimensions of the components are more enlarged than they actually are in order to clarify the present invention. It will be understood that terms, such as "first" or "second" may be used in the specification to describe various components but are not restricted to the above terms. The terms may be used to discriminate one component from another component. For instance, the first component may be named as the second component, and on the contrary, the second component may be also named as the first component within the scope of the present invention. The singular form of the components may be understood into the plural form unless otherwise specifically stated in the context.

It should be also understood that the terms of 'include' or 'have' in the specification are used to mean that there are characteristics, numbers, steps, operations, components, parts, or combinations of the steps, operations, components and parts described in the specification and there is no intent to exclude existence or possibility of other characteristics, numbers, steps, operations, components, parts, or combinations of the steps, operations, components and parts. In addition, when a portion, such as a layer, a membrane, a region, a plate or the like, is "on" another portion, it includes a case that the portion is "directly on" another portion, as well as a case that a further portion exists between the portions. On the other hand, if a portion, such as a layer, a membrane, a region, and a plate is "under" another portion, it includes not only a case that the portion is "directly below" another portion but also a case that a further portion exists between the portions.

Hereinafter, a biodegradable polymer microparticle for a filler, a manufacturing method thereof, a freeze-dried body including the same, and filler injection including the same according to preferred embodiments of the present disclosure will be described in more detail.

The biodegradable polymer microparticle contains a core and a shell, the core contains secondary particles including aggregates of a plurality of primary particles, and the shell has a raspberry shaped structure. An average particle diameter ($D_{50}$) of the secondary particle of the biodegradable polymer microparticle ranges from 20 to 200 µm.

The biodegradable polymer microparticle can be manufactured according to a spray drying technique or an emulsion method. Through the manufacturing method, microparticles having a spherical shape can be obtained. However, when the spherical biodegradable polymer microparticles are used, because of insufficient cell adsorption ability, it is required to improve the cell adsorption ability.

According to the present disclosure, provided is a method for manufacturing biodegradable polymer microparticles for a filler having improved cell adsorption ability due to improvement of the cell adsorption ability, and through the manufacturing method, biodegradable polymer microparticles having the surface of a raspberry-shaped structure was completed. The biodegradable polymer microparticle for a filler has a structure that is easy for cell adsorption since the surface area is increased greatly.

The biodegradable polymer microparticles having the raspberry shape can be manufactured according to a drowning-out crystallization method. In the present disclosure, the drowning-out crystallization method is to obtain biodegradable polymer microparticles by adding nonsolvent, in which biodegradable polymers are not dissolved, over a predetermined level and inducing supersaturation.

According to the method for manufacturing biodegradable polymer microparticles of the present disclosure, when supersaturation reaches the predetermined level, initial biodegradable polymer nuclei are formed, other nuclei or solutes are gathered around the biodegradable polymer nuclei to grow into microparticles. During the growth, fine spherical particles are agglomerated together to increase the volume. Finally, the microparticles form the raspberry shape and are manufactured into biodegradable polymer microparticles having a size suitable for a dermal filler.

The method for manufacturing biodegradable polymer microparticles for a filler includes: a first operation of mixing a first composition containing organic solvent miscible with water and biodegradable polymers and a second composition containing first surfactant and water, and preparing a third composition containing biodegradable polymer microparticle precursors for a filler and stirring them; a second operation of adding and mixing a fourth composition containing the first composition containing the biodegradable polymers, second surfactant, and water to the first operation product, and stirring them to prepare a fifth composition containing biodegradable polymer microparticles; and a third operation of separating the biodegradable polymer microparticles from the fifth composition. In the second operation, the feed rate of the fourth composition is faster than the feed rate of the second composition of the first operation, and the total content of the first surfactant and the second surfactant is parts by weight with respect to 100 parts by weight of the total content of the biodegradable polymer microparticles.

In the manufacturing method of the biodegradable polymer microparticles described above, water is nonsolvent which does not dissolve the biodegradable polymer microparticles according to the drowning-out crystallization method, and the organic solvent mixed with water is used as solvent for dissolving biodegradable polymer microparticles.

The first operation is an operation of forming the biodegradable polymer nuclei to obtain biodegradable polymer microparticle precursors.

The biodegradable polymer microparticle precursor has a shape that a secondary particle containing a plurality of primary particles is formed. An aggregate of the plurality of primary particles includes 100 primary particles or less, for instance, at least two primary particles, at least five primary particles, at least ten primary particles, at least 20 primary particles, at least 30 primary particles, at least 50 primary particles, or at least 75 primary particles. The aggregate of the plurality of primary particles according to an embodiment includes 10 to 50 primary particles.

In the second operation, a raspberry-shaped shell is formed on the surface of the biodegradable polymer microparticle precursor.

In the second operation, the feed rate of the fourth composition containing the second surfactant is faster than the feed rate of the third composition containing the first surfactant of the first operation. In the above condition, the biodegradable polymer microparticles having the raspberry-shaped shells can be obtained. If the feed rate of the fourth composition containing the second surfactant of the first operation gets slower than the feed rate of the third composition containing the first surfactant of the first operation, since spherical biodegradable polymer microparticles are obtained, it does not provide an effect of increasing the surface area.

In the present disclosure, the total content of the first surfactant and the second surfactant is 30 to 50 parts by weight, 32 to 48 parts by weight, 33 to 45 parts by weight, or 30 to 40 parts by weight with respect to 100 parts by weight of the total content of the biodegradable polymer microparticles. When the total content of the surfactant is in the above-mentioned range, biodegradable polymer microparticles of a secondary particle state that are aggregates of primary particles can be obtained. If the content of the surfactant is less than 30 parts by weight, it is difficult to obtain the secondary particles obtained by aggregating the primary particles. If the content of the surfactant exceeds 50 parts by weight, it is not preferable since the biodegradable microparticles overgrow.

The stirring speed of the second operation may be slower than the stirring speed of the first operation. When having the stirring speed, biodegradable microparticles having a desired structure can be obtained.

In the second operation, the content of the second surfactant is more than the content of the first surfactant in the first operation. The content of the first surfactant in the first operation is 5 to 20 parts by weight, 7 to 20 parts by weight, 8 to 20 parts by weight, 9 to 20 parts by weight or 10 to 20 parts by weight with respect to 100 parts by weight of the total content of the biodegradable polymer microparticles, and the content of the second surfactant in the second operation is 25 to 30 parts by weight, 26 to 29 parts by weight, or 27 to 28 parts by weight with respect to 100 parts by weight of the total content of the biodegradable polymer microparticles. Here, the total content of the first surfactant and the second surfactant is controlled to be 30 to 50 parts by weight with respect to 100 parts by weight of the total content of the biodegradable polymer microparticles.

In the manufacturing method of the present disclosure, it is controlled that the reaction temperature in the first operation, the second operation, and the third operation is 20 to 25° C., the stirring speed is 300 to 600 rpm, 300 to 550 rpm, 300 to 500 rpm, 310 to 590 rpm, 320 to 580 rpm, or 350 to 570 rpm, and the pH ranges from 4 to 6 or from 5 to 5.5. The manufacturing method of the present disclosure can obtain biodegradable polymer microparticles for a filler in the form of a raspberry shape which has a wide surface area and easy cell adsorption when the reaction temperature, the stirring speed, and the pH are in the above-mentioned ranges.

The biodegradable polymer microparticles obtained according to the manufacturing method are biodegradable polymer microparticles having a core and a shell containing secondary particles which are aggregates of primary particles, wherein the shell includes biodegradable polymer microparticles having a raspberry-like structure, and the average particle diameter ($D_{50}$) of the secondary particles is 20 to 200 μm. The biodegradable polymer microparticles for a filler have the above-mentioned average particle diameter, thereby facilitating storage and improving workability when filler injection is manufactured using the biodegradable polymer microparticles.

In the present specification, the "raspberry-like" structure has a large surface area. The raspberry-like structure occupies 80% by volume or less, 70% by volume or less, 60% by volume or less, or 45% by volume to 55% by volume of the core surface. The raspberry-like structure has a smooth surface and has a rounded corner. Therefore, when using the biodegradable polymer microparticles, in the case that a filler containing biodegradable polymer microparticles having a non-round edge is used, it can prevent side effects of piercing the tissue in the body, thereby being very suitable for a dermal filler.

The core can contain secondary particles including aggregates of a plurality of primary particles. The average particle diameter of the primary particles is 3 to 15 μm, 3 to 13 μm, 4 to 12 μm, 5 to 11 μm, or 8 to 10 μm. The average particle diameter of the secondary particles is, for example, 20 to 180 μm, 20 to 160 μm, 20 to 150 μm, 30 to 120 μm, 80 to 150 μm, 80 to 120 μm, 80 to 100 μm, or 100 μm. When the average particle diameter of the primary particles and the secondary particles is in the above-mentioned range, the surface area gets wider, thereby enabling easy cell adsorption. The average particle diameter of the primary particles and the secondary particles can be confirmed through a scanning electron microscope (SEM) photograph.

The biodegradable polymer microparticles of the present disclosure have a suitable size for a filler, and can provide improved cell adsorption ability and increase the effect of self-collagen generation stimulation of a dermal filler by widening the surface area while maintaining a unique curved surface of the raspberry shape in a sphere-like shape.

The average particle diameter ($D_{50}$) of the biodegradable microparticles for filler is used in the same meaning as the average particle diameter of the secondary particles, and is 20 to 200 μm, 20 to 150 μm, 20 to 100 μm, 50 to 100 μm, 80 to 150 μm, 80 to 120 μm, 80 to 100 μm, or 100 μm. The particle diameter ($D_{10}$) of the biodegradable polymer microparticles is 10 to 30 μm, for example 20 μm, and the particle diameter ($D_{90}$) is 180 to 210 μm, 180 to 200 μm, 180 to 190 μm, or 180 μm.

In the present specification, $D_{90}$, $D_{50}$, and $D_{10}$ are measured by a laser diffraction scattering type particle size analyzer (PSA). $D_{10}$ is a size value corresponding to 10%, 50%, and 90% of the maximum value in the cumulative distribution of the particles, and is a particle size corresponding to $1/10$, $5/10$, $9/10$ when a particle size distribution curve that the relative cumulative amount of the particles by size is presented in a curve is measured and schematized and is divided into 10 pieces. The median diameter ($D_{50}$) based on the cumulative volume measured from the particle size distribution diagram is calculated, and the calculated median diameter is set as an average diameter.

The full width at half maximum (FWHM) of the particle distribution curve is less than 50 μm, e.g., less than 40 μm. As described above, the biodegradable polymer microparticles of the present disclosure have very excellent uniformity in size.

The span of the biodegradable polymer microparticles of the present disclosure is represented by the following formula 1.

$$\text{Span} = (D_{90} - D_{10})/D_{50} \qquad \text{[Formula 1]}$$

The span is less than 2, from 1.0 to 3.4, from 1.0 to 1.9, from 1.0 to 1.8, from 1.0 to 1.7, from 1.5 to 1.7, or 1.6. A filler injection having excellent dispersibility can be obtained when the span is in the above-described range.

The span value becomes larger as the distribution of the particles becomes wider, is closer to zero as the distribution is narrow.

Polymer microparticles for filler can have a size applicable to a filler when having the average particle diameter in the above-mentioned range. If the average particle diameter of the polymer microparticles is too small, the polymer microparticles can be searched by macrophages and may not act as a filler. If the average particle diameter of the biodegradable polymer microparticles exceeds 200 μm, the polymer microparticles are not suitable for injection. For example, if the average particle diameter of the polymer microparticles is excessively increased, the diameter of the injection needle required for filler injection is increased, thereby increasing side effects, such as pain, during scar and operation. In addition, in the case of the face filler, when being injected into the face, it is very important to accurately adjust the volume of the face, but it is difficult to accurately adjust the volume due to an increase of the filler. The size of the biodegradable polymer microparticles used in the face filler is 40 to 100 μm.

The biodegradable polymer microparticles of the present disclosure have more volume compared to the same mass according to the porosity since having pores. The total porosity of the biodegradable polymer microparticles is 2 to 85%, 3 to 83%, 4 to 82%, or 5 to 80%. The porosity in the core is 3 to 30% or 5 to 25%, and the porosity in the shell is 35 to 80% or 40 to 75%.

The core is 60 to 95% by volume, 65 to 92% by volume, or 70 to 90% by volume, and the shell is 5 to 40% by volume, 8 to 35% by volume, or 10 to 30% by volume. When the core and the shell satisfy the above-mentioned volume, a filler injection can be manufactured to facilitate cell adsorption.

The biodegradable polymer microparticles of the present disclosure contain first biodegradable polymer microparticles and second biodegradable polymer microparticles. In the case of the first biodegradable polymer microparticles, the content of biodegradable polymer microparticles in the core is higher than the content of biodegradable polymer microparticles in the shell, and a difference in the concentration between the biodegradable polymer microparticles in the core and the biodegradable polymer microparticles in the shell is 0.01 to 3% by weight. The second biodegradable polymer microparticles have biodegradable polymer microparticles with the same concentration in the core and the shell. The composition can be identified from FIG. 2. If the biodegradable polymer microparticles have the composition described above, filler injection which is easy to disperse and easy for cell adsorption can be manufactured.

The content difference between the biodegradable polymer microparticles in the core and the biodegradable polymer microparticles in the shell is, for example, 0.5 to 3% by weight, 0.6 to 2.9% by weight, 0.7 to 2.8% by weight, 0.9 to 2.7% by weight, 1 to 2.5% by weight, or 1 to 2% by weight.

The specific surface area of the biodegradable polymer microparticles for a filler of the present disclosure is 0.3 to 1 $m^2/g$. Through the specific surface area, filler injection capable of facilitating cell adsorption can be manufactured.

FIG. 1A schematically illustrates the structure of biodegradable polymer microparticle for a filler of the present disclosure.

A biodegradable polymer microparticle (1) for a filler has a structure containing a core 10 and a shell 11. A shell 11 having a raspberry shape is disposed on the surface of a core 10 as shown in FIG. 1A. The core 10 may contain secondary particles comprising a plurality of primary particles.

In the biodegradable polymer microparticles, the core 10 occupies 60 to 95% by volume, 65 to 92% by volume, or 70 to 90% by volume, and the shell 11 occupies 5 to 40% by volume, 8 to 35% by volume, or 7 to 35% by volume with respect to the entire.

Figure 1B:
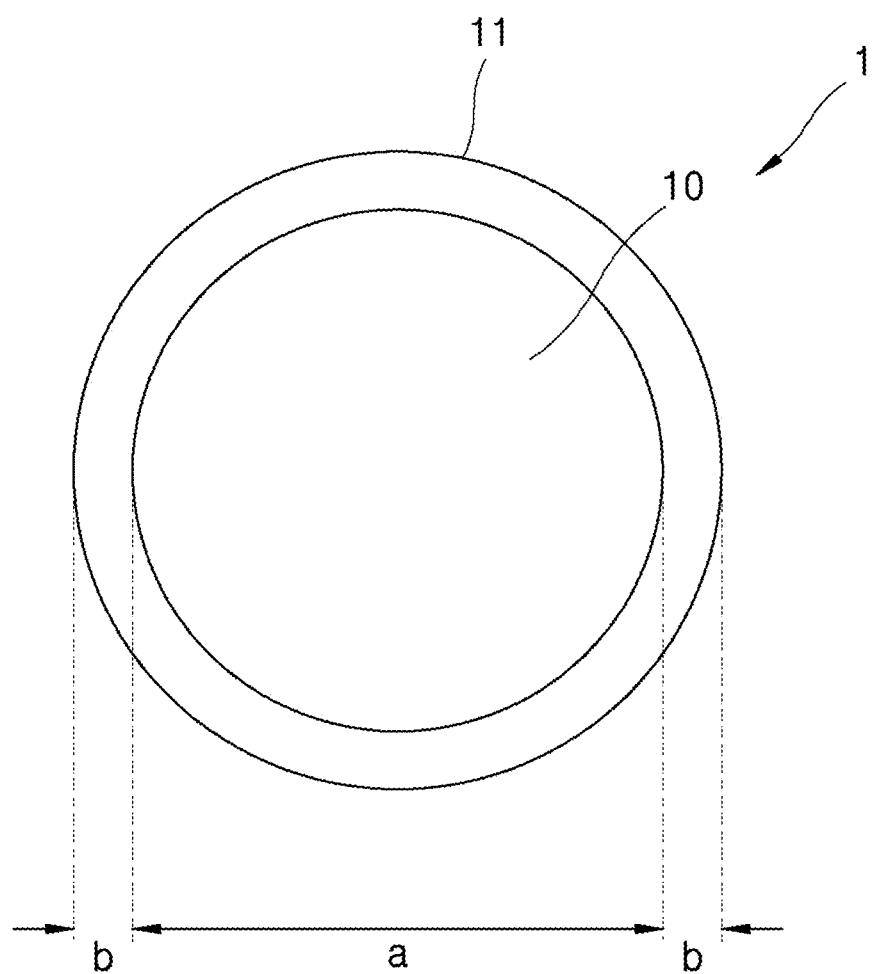
FIG. 1B is a diagram illustrating structures of a core and a shell in the biodegradable polymer microparticle of FIG. 1A.

In the present specification, the core can occupy a region (a) corresponding to 70 to 95% by length, 80 to 92% by length, or 90% by length from the center of the total distance between the center of the biodegradable polymer to the surface. Here, the total distance between the center of the biodegradable polymer to the surface represents a+2b in FIG. 1B. The shell may be a region (b) corresponding to 5 to 30% by length, 8 to 20% by length, 9 to 15% by length, for instance, 10% by length from the outermost surface of the total distance between the center of the biodegradable polymer to the surface.

The biodegradable polymer microparticles of the present disclosure may further include a dense intermediate layer between the core and the shell. The dense intermediate layer may be an intermediate layer having higher density than the core and the shell. The strength of the biodegradable polymer microparticles is excellent.

The present disclosure provides a freeze-dried body for a filler including the biodegradable polymer microparticles and a biocompatible carrier. Here, the biocompatible carrier is one or more selected from alginic acid and its salt, hyaluronic acid and its salt, carboxymethyl cellulose and its salt, dextran and its salt, collagen, Gelatin, and Elastin. The content of the biodegradable polymer microparticles and the biocompatible carrier in the freeze-dried body for a filler is 80:20 to 20:80. If the freeze-dried body contains the biocompatible carrier, the total content of the biocompatible carrier is 5 to 30 parts by weight, 5 to 20 parts by weight, or 5 to 10 parts by weight based on 100 parts by weight of the total content of the freeze-dried body for the filler.

The freeze-dried body is manufactured according to the following procedures.

The biodegradable polymer microparticles, the biocompatible carrier, and distilled water are dissolved to obtain a mixed solution. The mixed solution is poured into a mold and is pre-frozen to obtain a pre-frozen composition. The pre-freezing is performed at −75° C. to −50° C., for example, −75° C. to −65° C.

Subsequently, the pre-frozen composition can be manufactured by freeze-drying the mixed solution at −70° C. to −20° C., for example −45° C. to −20° C.

The cooling rate of the pre-freeze-drying and freeze-drying is −3° C./min to −2° C./min, or about −2.5° C./min.

The pre-freezing time and the freezing time vary depending on the pre-freezing temperature and the freezing temperature, but are carried out, for example, for 1 to 48 hours, 10 to 30 hours, or 15 to 24 hours.

The present disclosure also provides filler injection including at least one selected from biodegradable polymer microparticles for a filler, injection water, sterilized water, and distilled water.

The filler injection may further include a biocompatible carrier.

The content of the biodegradable polymer microparticles and the biocompatible carrier in the filler injection is 80:20 to 20:80. The total content of the biocompatible carrier is 5 to 30 parts by weight, 5 to 20 parts by weight, or 5 to 10 parts by weight based on 100 parts by weight of the total weight of the filler injection.

The biodegradable polymer of the present disclosure is one or more selected from groups consisting of polydioxanone (PDO), poly-lactic acid (PLA), poly-L-lactic acid (PLLA), poly-D-lactic acid (PDLA), poly-ε-caprolactone (PCL), Polyglycolic acid (PGA), a copolymer thereof, and a mixture thereof. The number average molecular weight (Mn) of the biodegradable polymer is 50,000 to 500,000 Daltons, or 50,000 to 200,000 Daltons. If the number average molecular weight of the biodegradable polymer is less than 50,000 Daltons, the decomposition speed of the biodegradable polymer microparticles may be increased not to be suitable as a biomaterial for a filler. If the number average molecular weight of the biodegradable polymer exceeds 500,000 Daltons, processing is difficult due to high viscoelasticity, thereby making it difficult to manufacture particles having uniform size and quality.

For example, the biodegradable polymer microparticles for a filler of the present disclosure are polydioxanone and have a weight average molecular weight of 50,000 to 200,000 Daltons.

Hereinafter, in the second operation of the method for manufacturing biodegradable polymer microparticles for a filler, which is a starting material used in manufacturing filler injection of the present disclosure, a feed rate of a fourth composition containing the second surfactant gets faster than the feed rate of the second composition of the first operation containing the first surfactant. The content of the surfactant is an element which affects the size control of the biodegradable polymer microparticles. According to the present disclosure, the size and microstructure of the biodegradable polymer microparticles are controlled by controlling the content and the feed rate of the first surfactant and the second surfactant.

In the method for manufacturing the biodegradable polymer microparticles of the present disclosure, the growth rate of the polymer microparticle particles in the second operation can be increased to be the same as or less than 20% of the growth rate of the polymer microparticles in the first operation. In addition, the injection amount of the biodegradable polymer microparticles growing the particles to control the growth rate can be increased by 15 to 35%, for example, about 25% in the second operation compared to the first operation.

According to the present disclosure, the present disclosure controls the feed rate of each composition and the content of the surfactant so as to obtain raspberry-shaped microparticles containing secondary particles formed by aggregating primary particles.

According to the manufacturing method described above, biodegradable polymer microparticles having an average particle diameter of 20 to 200 um suitable for a face filler and having improved particle diameter uniformity can be simply manufactured at a high yield.

The method for manufacturing biodegradable polymer microparticles for a filler according to the present disclosure will be described in detail as follows.

First, a first operation of mixing a first composition containing organic solvent miscible with water and biodegradable polymers and a second composition containing first surfactant and water, and preparing a third composition containing biodegradable polymer microparticle precursors for a filler and stirring them is carried out.

The first composition can be manufactured by dissolving the biodegradable polymers in the organic solvent. The biodegradable polymer containing the first composition is one or more selected from groups consisting of polydioxanone (PDO), poly-lactic acid (PLA), poly-L-lactic acid (PLLA), poly-D-lactic acid (PDLA), poly-ε-caprolactone (PCL), Polyglycolic acid (PGA), a copolymer thereof, and a mixture thereof. The copolymer may be, for example, a polylactic acid-glycolic acid copolymer, a polydioxanone-caprolactone copolymer, a folate-caprolactone copolymer, and the like. The biodegradable polymer is, for example, polydioxanone.

The number average molecular weight (Mn) of the biodegradable polymer containing the first composition is 50,000 to 500,000 Daltons, 50,000 to 300,000 Daltons, or 50,000 to 200,000 Daltons. If the number average molecular weight of the biodegradable polymer is less than 50,000 Daltons, the decomposition speed of the biodegradable polymer microparticles may be increased not to be suitable as a biomaterial for a filler. If the number average molecular weight of the biodegradable polymer exceeds 500,000 Daltons, processing is difficult due to high viscoelasticity, thereby making it difficult to manufacture particles having uniform size and quality.

The content of the biodegradable polymer containing the first composition is, for example, 0.1 to 20 wt %, 0.1 to 10 wt %, 1 to 10 wt %, 3 to 9 wt %, or 4 to 8 wt % with respect to the entire first composition. If the content of the biodegradable polymer containing the first composition is too low, manufacturing efficiency of the polymer microparticles may be reduced since the content of the biodegradable polymer containing the first composition is too low. When the content of the biodegradable polymer containing the first composition is too high, it is difficult to obtain polymer microparticles having a uniform size.

The "organic solvent miscible with water" is organic solvent that is completely or partially mixed with water. The organic solvent miscible with water means organic solvent that does not form a separate phase distinct from, for example, water. The organic solvent miscible with water is solvent having solubility of, for example, 3 g or more, 5 g or more, 10 g or more, 20 g or more, or 50 g or more, with respect to, for example, 100 g of water at 20° C.

The organic solvent containing the first composition may be one or more selected from the groups consisting of, for example, 1,1,1,3,3,3-Hexafluoro-2-propanol (HFIP), acetone, acetonitrile, acetic acid, dioxane, ethanol, methanol, isopropyl alcohol (IPA), propanol, tetrahydrofuran (THF), pentane, and mixtures thereof. For example, if polydioxanone is used as a biodegradable polymer containing the first composition, alcohol with C1 to C6 that 3 to 13 fluorine atoms are substituted, for example, 1,1,1,3,3,3-hexafluoro-2-propanol, can be used as organic solvent for dissolving polydioxanone.

The boiling point of the organic solvent containing the first composition may be, for example, 10° C. to 100° C., 20 to 90° C., or 30 to 80° C. The organic solvent can be easily volatilized since having such a range of the boiling point. If the boiling point of the organic solvent is too low, it is difficult to maintain the liquid phase, and if the boiling point of the organic solvent is too high, evaporation of the organic solvent becomes difficult and the content of the residual solvent is increased, thereby deteriorating biocompatibility of the biodegradable polymer microparticles.

The content of the organic solvent containing the first composition is, for example, 50 to 99.9 wt %, 60 to 99.9 wt %, 70 to 99.9 wt %, 80 to 99.9 wt %, or 90 to 99.9 wt %, with respect to the total weight of the first composition. If the content of the organic solvent containing the first composition is too low, uniform polymer microparticles may not be obtained since the viscosity of the first composition is increased. If the content of the organic solvent containing the first composition is too high, the manufacturing efficiency of the polymer microparticles is reduced since the content of the polymer microparticles generated from the first composition is too low.

The second composition containing the first surfactant and water can be manufactured by dissolving the first surfactant in at least one selected from water and alcohol.

The aqueous solution is a composition containing water, and is not necessarily limited to 100%. In the case of the second composition, the content of water in the solvent is, for example, at least 50 wt %, at least 60 wt %, at least 70 wt %, at least 80 wt %, or at least 90 wt %. The solvent containing the second composition is, for example, water.

The first surfactant may be at least one selected from a water-soluble polymer, such as Polyvinyl alcohol, polyoxyethylene sorbitan, and salts thereof, and water-soluble monomers, such as soybean Lecithin, monoglyceride, and the like.

The content of the first surfactant in the second composition can be, for example, 1 to 10 wt %, 3 to 9 wt %, or 4 to 8 wt % with respect to the entire second composition. If the content of the first surfactant is too low, interfacial activity of the surfactant is weakened, thereby making it difficult to manufacture polymer microparticles having a uniform size. If the content of the first surfactant is too high, since the size of the polymer microparticles is excessively reduced, it cannot act as a filler as being searched by macrophages in the living body, or the size of the polymer microparticles can increase due to generation of agglomeration of the polymer microparticles. When a polyvinyl alcohol, which is a water-soluble polymer, is used as the first surfactant containing the second composition, water or mixture of water and alkyl alcohol can be used as the solvent in which polyvinyl alcohol is dissolved.

When the water-soluble polymer is used as the first surfactant, the number average molecular weight of the water-soluble polymer may be, for example, 50,000 to 200,000 Daltons, 70,000 to 170,000 Daltons, or 100,000 to 150,000 Daltons. If the number average molecular weight of the water-soluble polymer is less than 50,000 Daltons, the interface activity can be lowered. If the number average molecular weight of the water-soluble polymer exceeds 200,000 Daltons, it may be difficult to form uniform polymer microparticles due to high concentration.

The second composition may further include other surfactants other than the first surfactant described above. The other surfactants are anionic surfactants, cationic surfactants or amphoteric surfactants. The surfactant is one or more selected from polyoxyethylene sorbitan monolaurate (Tween 20), polyoxyethylene sorbitan monopalmitate (Tween 40), polyoxyethylene sorbitan monostearate (Tween 60), polyoxyethylene sorbitan monooleate (Tween 80), and polyoxyethylene sorbitan trioleate (Tween 85). The second composition can produce polymer microparticles having a uniform particle size suitable for a filler at a high yield even when the second composition does not additionally contain other surfactants.

The pH of the second composition may be at least 5.0, at least 5.5, at least 6.0, or at least 6.5. The pH of the second composition may be, for example, 5.0 to 8.0, 5.0 to 7.5, 5.0 to 7, or 5 to 6.5. The produce polymer microparticles having a uniform size can be manufactured at a high yield since having the pH in the above-mentioned range.

The content of the first surfactant in the third composition is 5 to 20 parts by weight based on 100 parts by weight of the biodegradable polymer microparticle for filler.

In the operation of preparing the third composition, the organic solvent and water can be mixed in a ratio of 50 to 200 parts by volume of water containing the second composition with respect to 100 parts by volume of the organic solvent containing the first composition. For example, the mixing volume ratio of the organic solvent and water is 1:0.5 to 1:2, 1:0.6 to 1:1.8, 1:0.7 to 1:1.6, 1:0.7 to 1:1.5, 1:0.8 to 1:1.3, or 1:0.8 to 1:1.2. In the operation of preparing the mixture, since 100 parts by volume of the organic solvent and 50 to 200 parts by volume of water are mixed, the present disclosure is remarkably reduced in the used amount of water compared to a conventional manufacturing method in which 100 parts by volume of the organic solvent and 800 parts by volume of water are mixed. In addition, in the conventional manufacturing method in which 100 parts by volume of the organic solvent and 800 parts by volume of water are mixed, it is difficult to manufacture the polymer microparticles having a uniform particle diameter since rapid precipitation of the biodegradable polymer is performed by adding a first composition to an excess of water, thereby making it difficult to manufacture the polymer microparticles having a uniform particle diameter. On the other hand, in the manufacturing method of the present disclosure in which organic solvent and water are mixed at a similar volume ratio, polymer microparticles having a uniform particle diameter can be easily manufactured since the precipitation of the biodegradable polymer develops slowly. Moreover, compared to the prior art using an excess amount of solvent, the amount of solvent used is remarkably reduced, and the polymer microparticles can be manufactured more easily.

In the operation of preparing the third composition, mixing the first composition and the second composition and stirring the mixture can be performed sequentially or substantially simultaneously. For example, the first composition and the second composition are put into a container in which the agitator rotates sequentially or simultaneously to prepare the mixture, and at the same time, the mixture is stirred.

Stirring the first composition and the second composition may be performed at 300 to 500 rpm, or 300 to 500 rpm. If stirring (e.g., stirring speed, RPM) of the mixture is too slow, mixing the first composition and the second composition may not be smoothly performed. If stirring (e.g., stirring speed, RPM) of the mixture is too fast, the uniformity of the particle size of the polymer microparticles may be reduced.

Stirring the mixture may be performed at least one day, namely, 24 hours. Since stirring the mixture is performed for a long time and the organic solvent volatilizes slowly, the biodegradable polymer can be gradually precipitated into polymer microparticles in the uniform condition. Therefore, the uniformity in the particle size of the polymer microparticles can be improved. Since the stirring the mixture is performed at a low speed of 800 rpm or more, the precipitation of the polymer microparticles may not be sufficiently performed if the stirring time is less than one day, namely, 24 hours. The stirring time of the mixture may be, for example, 1 to 10 days, 2 to 9 days, 3 to 8 days, 3 to 7 days, or 4 to 6 days. If the stirring time of the mixture is excessively increased, the manufacturing efficiency of the polymer microparticles can be lowered.

After that, a second operation of adding and mixing a fourth composition containing the first composition, which contains the biodegradable polymers and the organic solvent miscible with water, the second surfactant, and water to the product obtained according to the first operation, and stirring them to prepare a fifth composition containing biodegradable polymer microparticles for a filler is carried out.

In the second operation, the first composition is omitted since being equal to the first composition of the first operation. Except that the fourth composition uses not the first surfactant but the second surfactant, the second surfactant is the same as the second composition of the first operation. The second surfactant may be the same as the first surfactant or different from the first surfactant.

Next, a third operation of separating the filler biodegradable polymer microparticles from the fifth composition is carried out. The method of separating the filler polymer microparticles from the fifth composition uses, for example, filtration, precipitation, washing, and the like.

Distilled water is put into the separated biodegradable polymer microparticles, the mixture is stirred at 100 to 1000 rpm for 1 to 24 hours, and a washing process of removing the distilled water can be performed at least once. The impurities remaining in the polymer microparticles can be effectively removed by the washing process.

In the second operation, the feed rate of the fourth composition gets faster than the feed rate of the third composition of the first operation. The feed rate of the third composition in the first operation is 50 to 100 ml/min, and the feed rate of the fourth composition in the third operation is 90 to 120 ml/min.

The stirring speed of the second operation gets slower than the stirring speed of the first operation. The stirring speed of the second operation is 300 to 400 rpm or 350 to 400 rpm, and the stirring speed of the first operation is 400 to 500 rpm. In addition, the content of the surfactant in the second operation may be increased more than the content of the surfactant in the first operation.

The content of the first surfactant in the first operation is 5 to 20 parts by weight with respect to 100 parts by weight of the total content of the biodegradable polymer microparticles, and the content of the second surfactant in the second operation is 25 to 30 parts by weight with respect to 100 parts by weight of the total content of the biodegradable polymer microparticles.

The feed rate of the first composition in the first operation is 3.0 to 5.0 ml/min, for instance, 4.3 ml/min. The second operation is performed in the condition that the growth speed of particles is increased by 20% or more compared with the first operation. The feed rate of the first composition in the second operation increases 1.5 times or more, for example, form 1.5 times to 2.5 times, compared with the feed rate of the first composition of the first operation. In order to increase the growth speed of particles of the second operation compared with that of the first operation, the method further includes an operation of diluting concentration of reaction mixture in a reactor. Furthermore, the stirring speed of the reaction mixture in the second operation gets slower than the stirring speed of the reaction mixture in the first operation. As described above, when the stirring speed is reduced, the desired biodegradable polymer microparticles can be manufactured without formation of additional particles.

The manufacturing method of the present disclosure may not include stabilizing in stabilizer or in stabilizing solution. Therefore, manufacturing the polymer microparticles becomes simpler. The conventional method consumes lots of time and solvent since including an operation of stabilizing in an excess of alcohol or an excess of surfactant aqueous solution for a long time in order to stabilize or age the manufactured polymer microparticles. In contrast, the present disclosure prepares can remarkably reduce manufacturing time and use of solvent since preparing the third composition including polymer microparticles and obtaining polymer microparticles by separating and/or washing the polymer microparticles without the stabilizing operation.

In the operation of selecting polymer microparticles having an average particle diameter of 20 to 200 μm or 20 to 100 μm from the polymer microparticles separated during manufacturing of the biodegradable polymer microparticles, the biodegradable polymer microparticles can be classified by sizes in dry or wet type, for example, using a size sizing machine. In the case of wet type sieving, freeze-drying is additionally performed to classify the polymer microparticles after removing moisture. However, the method for manufacturing polymer microparticles of the present disclosure can produce particles having a size in the range of 25 to 75 μm at a high yield without such a classification process.

The biodegradable polymer microparticle for a filler is provided to be used for wrinkle improvement, facial molding, body molding, male prosthesis, or urinary incontinence treatment.

In another aspect of the present invention, provided is a manufacturing method of filler injection according to an embodiment.

The filler injection can be manufactured through the manufacturing method including the operations of: preparing biodegradable polymer microparticles for a filler having an average particle diameter of 20 to 200 μm or 20 to 100 μm; manufacturing biodegradable polymer microparticles surface-treated by performing the operations of surface-treating the biodegradable polymer microparticles with plasma or surface-treating the biodegradable polymer microparticles with a base; and hydrating the surface-treated biodegradable polymer microparticles in one or more selected from injection water, sterilized water, and distilled water.

As described above, the biodegradable polymer microparticles for filler are prepared. The prepared biodegradable polymer microparticles and the biocompatible carrier are mixed to prepare a sixth composition.

The sixth composition can be manufactured by adding, for example, biodegradable polymer microparticles and biocompatible carriers to solvent. For example, the sixth composition can be manufactured by adding a biocompatible carrier to an aqueous solution containing biodegradable polymer microparticles. Water or a mixed solution of water and an alkyl alcohol may be used as the solvent. The fourth composition can evenly disperse the mixture solution of high viscosity by using, for example, a three-roll mill or the like.

The sixth composition may further include additional components, such as a bioactive material and a local anesthetic, according to use purposes. The added components are not necessarily limited thereto, and the components and contents added according to the use purposes can be determined.

The biocompatible carrier contained in the sixth composition may include one or more selected from the groups consisting of alginic acid and its salt, hyaluronic acid and its salt, carboxymethyl cellulose and its salt, dextran and its salt, collagen, gelatin, and elastin. The biocompatible carrier may be, for example, carboxymethyl cellulose. The viscosity of the aqueous solution containing 0.5 to 3 wt % of the biocompatible carrier can be, for example, 1,000 to 10,000 cPs at 25° C. The biocompatible carrier can control the viscosity of the second composition since having the viscosity.

The content of the biodegradable polymer microparticles contained in the sixth composition may be 10 to 80 wt %, 10 to 50 wt %, 10 to 30 wt %, or 15 to 30 wt % with respect to the entire fifth composition. If the content of the biodegradable polymer microparticles is less than 10 wt %, it may be difficult to disperse evenly due to low concentration. If the content of the biodegradable polymer microparticles exceeds 80 wt %, it makes freeze-drying and mixing with the biocompatible carriers difficult due to the low moisture content.

The ratio of the biodegradable polymer microparticles contained in the sixth composition to the biocompatible carrier may be 20:80 to 80:20 in weight ratio. If the ratio of the biodegradable polymer microparticles to the biocompatible carrier is out of the above-mentioned range, it is difficult to evenly disperse the biodegradable polymer microparticles in an appropriate concentration by the biocompatible carrier. The fourth composition can be used as injection as it is.

The present disclosure can be used as injection by hydrating at least one selected from injection water, sterilized water, and distilled water.

The biodegradable polymer filler can be, for example, a spherical porous particle, but the present disclosure is not limited thereto, and can be selected according to required conditions. The biodegradable polymer filler may be a spherical porous particle having the surface of a raspberry-shaped structure, and can be quickly hydrated in water or the like due to capillary phenomenon by having porosity.

The biodegradable polymer microparticles for a filler may have a density of, for example, 0.2 to 0.9 g/cm$^3$, 0.2 to 0.8 g/cm$^3$, 0.2 to 0.7 g/cm$^3$, 0.2 to 0.6 g/cm$^3$, or 0.2 to 0.5 g/cm$^3$. The biodegradable polymer microparticles for a filler can be easily and quickly hydrated in water or the like by applying the density of the above-mentioned range.

The biodegradable polymer microparticles may further include an operation of sterilizing the spherical porous particles after preparing the spherical porous particles by removing moisture.

Sterilization is performed by gamma-ray sterilization, ethylene oxide sterilization, or decompression sterilization, but is not limited thereto, and any sterilizing method used in the relevant technical field is applicable.

The biodegradable polymer microparticle is provided to facilitate the manufacture of injection by rapidly performing hydration since the biodegradable polymer microparticles are formed in a raspberry shape. The injection manufactured by the method has viscosity of 8,000 to 30,000 cPs at 25° C. and a compressive force of 5N to 12N.

Alternatively, the biodegradable polymer microparticles may be in the form of dry powder.

Hereinafter, examples of the present disclosure will be described in more detail. The following examples are just illustrated for assisting understanding of the present disclosure, and the scope of the present disclosure is not limited thereto.

(Manufacturing Biodegradable Polymer Microparticles)

Preparation Example 1: Preparation of Polydioxanone Microparticles

1) First operation: Content of PVA: 10 parts by weight (based on 100 parts by weight of PDO), Feed rate of second composition containing PVA: 5.0 L/hr, Feed rate of first composition containing PDO: 2.0 L/hr, Stirring speed: 500 rpm Polydioxanone (PDO) with intrinsic Viscosity (IV) of 1.55 dL/dg and number average molecular weight of 100,000 Daltons as biodegradable polymer was dissolved in Hexafluoroisopropanol (HFIP), which is an organic solvent, to prepare a first composition containing Hexafluoroisopropanol and 3.3% by weight of PDO.

A second composition with about pH 5.5, which was 3.3 wt % PVA aqueous solution in which polyvinyl alcohol (PVA) with number average molecular weight of 130,000 Daltons was dissolved in distilled water, was prepared as the first surfactant.

The first composition and the second composition were mixed at a volume ratio of 1:1 to prepare a mixture. The prepared mixture was stirred at 400 rpm for 5 days to remove the organic solvent, thereby obtaining a third composition containing polymer microparticles.

The content of PVA in the third composition was 10 parts by weight based on 100 parts by weight of PDO. After stirring, the third composition was left as it was for 24 hours so that the PDO microparticles were settled. After that, the supernatant was removed as much as possible. A sufficient amount of purified water was added and stirred for one hour, and then, was left as it was for 24 hours. The above process was repeated three times.

2) Second operation: Content of PVA: 25 parts by weight (based on 100 parts by weight of PDO), Feed rate of fourth composition containing PVA: 6.5 L/hr, Feed rate of first composition containing PDO: 2.0 L/hr, Stirring speed: 400 rpm A first composition containing PDO and HFIP and a fourth composition containing PVA, which was second surfactant, and water were added and mixed to the product obtained according to the first operation so as to obtain a fifth composition containing biodegradable polymer microparticles. The PVA content in the fourth composition was 6.6% by weight. The first composition has the same composition as the first composition used in the first operation. The PVA content as the second surfactant in the fourth composition was 25 parts by weight based on 100 parts by weight of PDO.

3) Third Operation

After stirring, the polymer microparticles were left as they were for 24 hours so that the polymer microparticles were settled, and then, the supernatant was removed, and the polymer microparticles were separated.

Purified water was added to the separated polymer microparticles and then was stirred again to be washed. The washing operation was performed three times to manufacture polymer microparticles for a filler.

The polymer microparticles for a filler were placed on a sieve having holes of 20 μm size for at least six hours to primarily remove water. Then, completely dried microparticles were obtained through a drying process in a vacuum dryer (5 Pa or less) for at least two days.

The dried microparticles were obtained when the PDO microparticles having the size range as illustrated in the following Table 1 were sorted through various sizes of sieve. The total content of PVA in the preparation example 1 was 30 parts by weight based on 100 parts by weight of biodegradable polymer microparticles.

Preparation Example 2

Except that the stirring speed of the first operation was 400 rpm and the stirring speed of the second operation was 350 rpm, biodegradable polymer microparticles were manufactured in the same manner as in the preparation example 1. In the preparation example 2, the total amount of PVA was 30 parts by weight based on 100 parts by weight of the biodegradable polymer microparticles.

Preparation Example 3

Except that the content of PVA in the first operation was 20 parts by weight based on 100 parts by weight of PDO, and the content of PVA was changed to 30 parts by weight in the second operation, biodegradable polymer microparticles for filler were manufactured in the same manner as in the preparation example 1. The total content of PVA in the preparation example 3 was 50 parts by weight based on 100 parts by weight of biodegradable polymer microparticles.

Preparation Examples 4 and 5

Except that Poly-L-L-Lactic acid (PLLA) with inherent viscosity (IV) of 0.8 to 1.2 dL/dg and number average molecular weight of 80,000 to 120,000 Daltons, and Poly-ε-caprolactone (PCL) with inherent viscosity (IV) of 0.8 to 1.0 dL/dg and number average molecular weight of 80,000 to 110,000 Daltons were used, the biodegradable polymer microparticles for a filler were manufactured in the same manner as in the preparation example 1.

Comparative Preparation Example 1

Polydioxanone (PDO) with intrinsic Viscosity (IV) of 1.55 dL/dg and number average molecular weight of 100,000 Daltons as biodegradable polymer was dissolved in Hexafluoroisopropanol (HFIP), which is an organic solvent, to prepare a first composition containing Hexafluoroisopropanol and 6% by weight of PDO.

A second composition with about pH 5.5, which was 9.1 wt % PVA aqueous solution in which polyvinyl alcohol (PVA) with number average molecular weight of 130,000 Daltons was dissolved in distilled water, was prepared as the surfactant.

The first composition and the second composition were mixed at a volume ratio of 1:1 to prepare a mixture. The prepared mixture was stirred at 400 rpm for 5 days to remove the organic solvent, thereby obtaining a third composition containing polymer microparticles.

After stirring, the polymer microparticles were left as they were for 24 hours so that the polymer microparticles were settled, and then, the supernatant was removed, and the polymer microparticles were separated.

Purified water was added to the separated polymer microparticles and then was stirred again to be washed. The washing operation was performed three times to manufacture polymer microparticles for a filler.

Comparative Preparation Example 2

Except that the content of PVA in the first operation was 5 parts by weight based on 100 parts by weight of PDO, and the content of PVA in the second operation was 10 parts by weight based on 100 parts by weight of PDO, biodegradable polymer microparticles for a filler were manufactured in the same manner as in the preparation example 1. The total content of PVA in the first operation and the second operation was 15 parts by weight.

Comparative Preparation Example 3

Except that the content of PVA in the first operation was 10 parts by weight based on 100 parts by weight of PDO, and the content of PVA in the second operation was 10 parts by weight based on 100 parts by weight of PDO, biodegradable polymer microparticles for a filler were manufactured in the same manner as in the preparation example 1. The total content of PVA in the first operation and the second operation was 20 parts by weight.

Comparative Preparation Example 4

Except that the feed rate of the second composition (feed rate of PVA) in the first operation was 6.5 L/hr and the feed rate of the fourth composition (feed rate of PVA) in the second operation was 5.0 L/hr, biodegradable polymer microparticles for a filler were manufactured in the same manner as in the preparation example 1. According to the comparative preparation example 4, the feed rate of the fourth composition in the second operation was reduced compared to the feed rate of the second composition of the first operation.

(Manufacturing Filler Injection)

Example 1

Polydioxanone microparticles for a filler manufactured in the preparation example 1 were mixed with sterilized injectable water so as to prepare a mixed composition.

The content of the polydioxanone microparticles contained in the mixed composition was 30 wt %.

The mixed composition can be used as injection as it is, or can be used as injection by hydrating the powder which was obtained through freeze-drying of the mixed composition, in sterilized injectable water.

Examples 2 and 3

Except that polydioxanone microparticles manufactured in the preparation example 2 and the preparation example 3 were used instead of the polydioxanone microparticles manufactured in the preparation example 1, filler injection was manufactured in the same manner as the example 1.

Examples 4 and 5

Except that poly-L-lactic acid microparticles and polycaprolactone microparticles of the preparation examples 4-5 were used instead of the polydioxanone microparticles of the preparation example 1 as biodegradable polymer microparticles, filler injection was manufactured in the same manner as the example 1.

Comparative Examples 1 to 4

Except that polydioxanone microparticles manufactured in the comparative preparation examples 1 to 4 were used instead of the polydioxanone microparticles manufactured in the preparation example 1, filler injection was manufactured in the same manner as the example 1.
(Manufacturing Freeze-Dried Body)

Example 6

4 g of polydioxanone microparticles for a filler manufactured in the preparation example 1 were dispersed in a solution in which 1 g of carboxymethyl cellulose (CMC) with reference viscosity of 1125 to 2100 cP based on a 2% solution was completely dissolved, so as to manufacture a mixed solution.

A predetermined amount of the mixed solution was poured into a semispherical mold having a height of 5 mm. After that, the mold was pre-frozen in a freezer having internal temperature of −75° C. for 24 hours, and then, was pre-freeze-dried for 24 hours in a freeze drier so as to manufacture a pre-freeze-dried body for a filler.

The pre-freeze-dried body was placed in the freezer a having internal temperature of −20° C., and then, was freeze-dried for 24 hours in the freeze drier so as to manufacture a freeze-dried body for a filler. The content of the CMC in the freeze-dried body was 20% by weight based on 100% by weight of the freeze-dried body.

Examples 7 and 8

Except that polydioxanone microparticles manufactured in the preparation examples 2 and 3 were used instead of the polydioxanone microparticles manufactured in the preparation example 1, a freeze-dried body was manufactured in the same manner as the example 1.

Comparative Examples 5 to 8

Except that polydioxanone microparticles manufactured in the comparative preparation examples 1 and 4 were used instead of the polydioxanone microparticles manufactured in the preparation example 1, a freeze-dried body was manufactured in the same manner as the example 1.

Evaluation Example 1: Scanning Electron Microscope Analysis

Figure 2A:
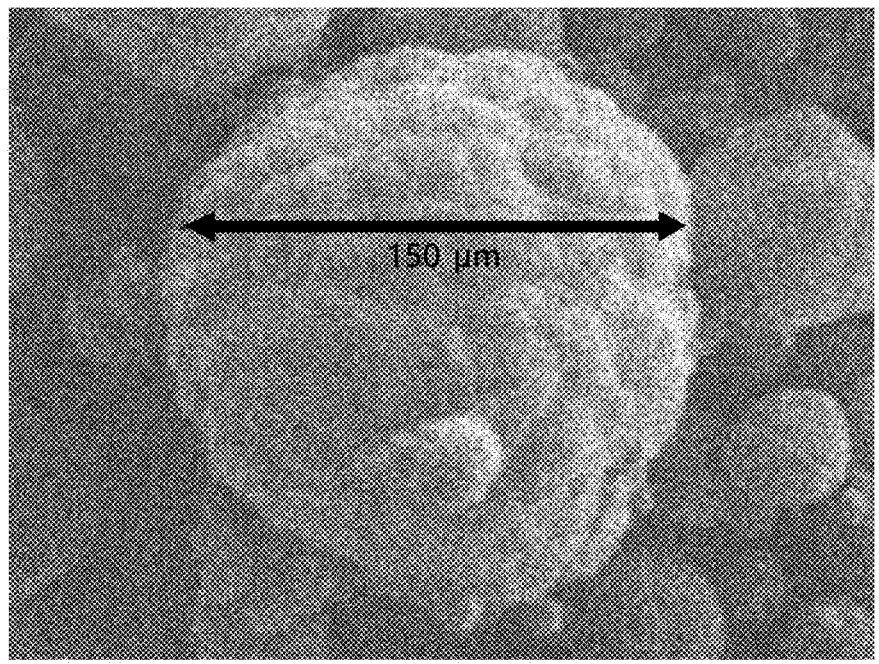
FIGS. 2A to 2C are scanning electron microscope images of a PDO microparticle of a preparation example 1, and PDO microparticles of comparative preparation examples 1 and 2.
Figure 2B:
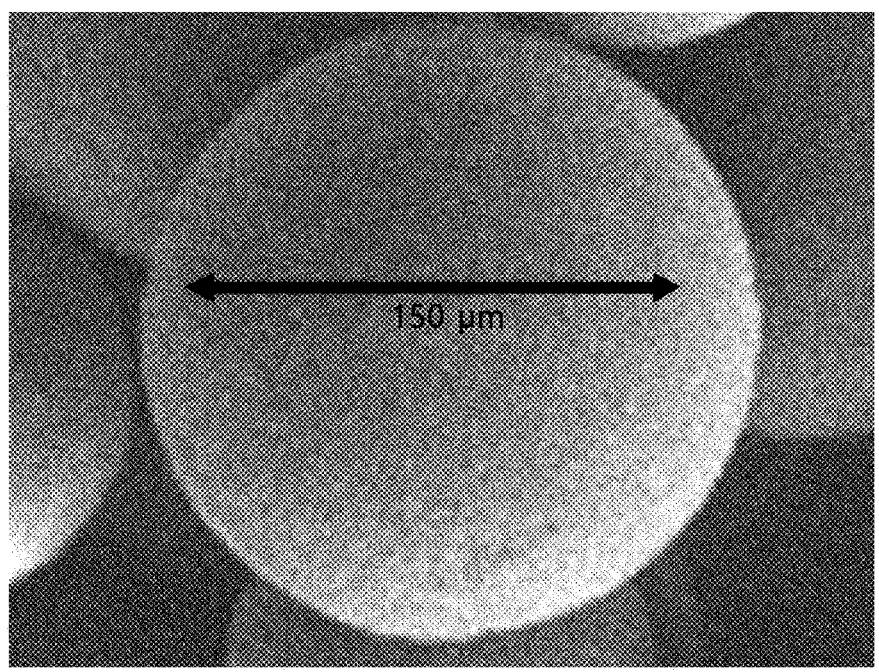
Figure 2C:
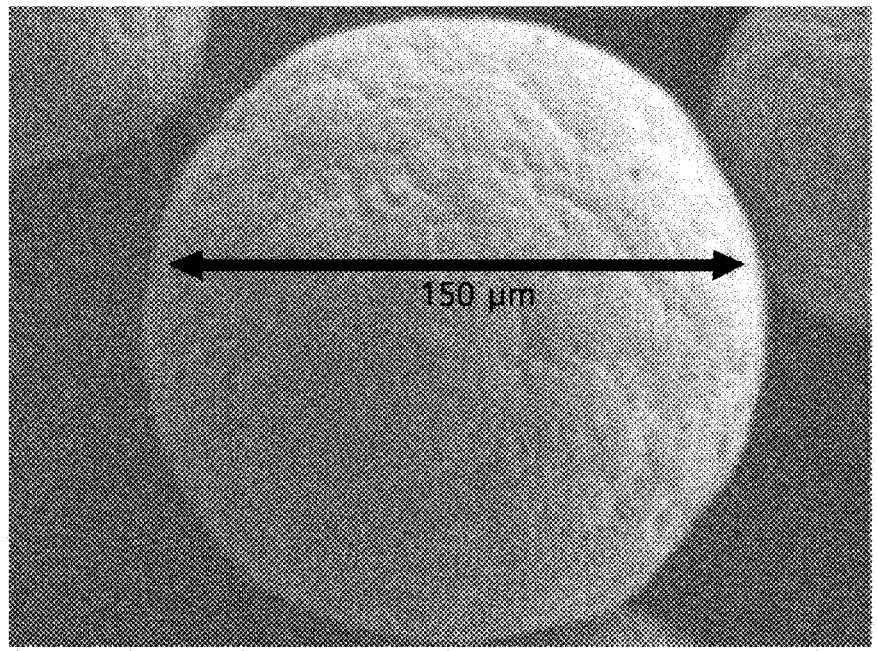

Scanning electron microscope images of the polymer microparticles manufactured in the preparation example 1 and the comparative preparations examples 1 and 2 were respectively illustrated in FIGS. 2A, 2B, and 2C.

The PDO polymer microparticles of the comparative preparations examples 1 and 2 were spherical particles having a smooth surface as illustrated in FIGS. 2B and 2C.

However, the PDO microparticles of the preparation example 1 contain secondary particles which were aggregates of a plurality of primary particles as illustrated in FIG. 2A, and PDO microparticles having a raspberry-shaped structure were present on the surfaces of the secondary particles. As such, the PDO microparticles of the preparation example 1 had a particle form, which was very different from the PDO microparticles of the comparative preparation examples 1 and 2. Additionally, in the PDO microparticles of the preparation example 1, the average particle diameter of the primary particles of the core was about 10 μm and the average particle diameter of the secondary particles was about 150 μm.

Evaluation Example 2: Optical Microscope Analysis

An optical microscope analysis with respect to the PDO microparticles obtained according to the preparation example 1 was performed. The optical microscope analysis result was as shown in FIG. 3.

Figure 3:
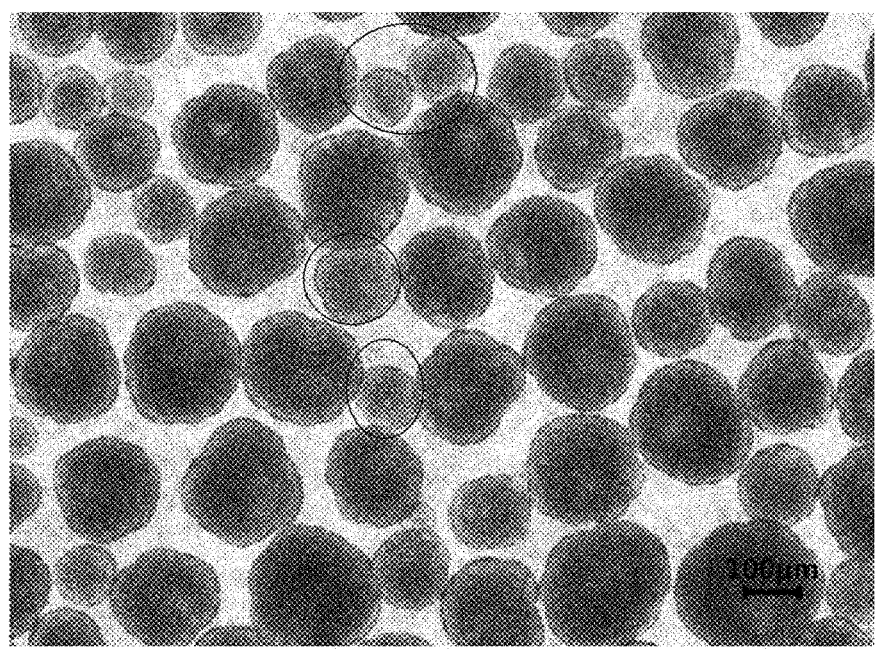
FIG. 3 is a view showing an analysis result of an optical microscope in relation to PDO microparticles obtained according to the preparation example 1.

Referring to FIG. 3, it was confirmed that the polymer microparticles of the example 1 had a structure including a core and a shell as a result of the optical microscope analysis, and the shell had a raspberry shape. In addition, the relative volume ratio of the core and the shell could be confirmed through the optical microscope analysis. The core was 70-80% by volume, specifically about 75% by volume, and the shell was 20-30% by volume, specifically about 25% by volume.

Moreover, referring to FIG. 3, it was confirmed that the PDO microparticles of the preparation example 1 contained a first biodegradable microparticle (A) having a concentration difference in the core and the shell, and a second biodegradable microparticle (B) having substantially the same concentration in the core and the shell.

The second biodegradable microparticle (B) represented the particles existing in the same area in FIG. 3. The content of the second biodegradable microparticles (B) was about 6 to 8% by weight based on the total weight of the first biodegradable microparticles (A) and the second biodegradable microparticles (B). The content of the second biodegradable microparticles (B) was confirmed through the optical microscope analysis.

Evaluation Example 3: Comparison of Surface Area

In the case of the biodegradable polymer microparticles for a filler of the example 1, through an image analysis, it was estimated that a ratio of a diameter of a protruding hemisphere and a diameter ratio of the entire particle was 1:6, and the ratio was calculated and was compared with a surface area of a smooth sphere. Examples of such calculations are illustrated in FIGS. 4 and 5.

Figure 4:
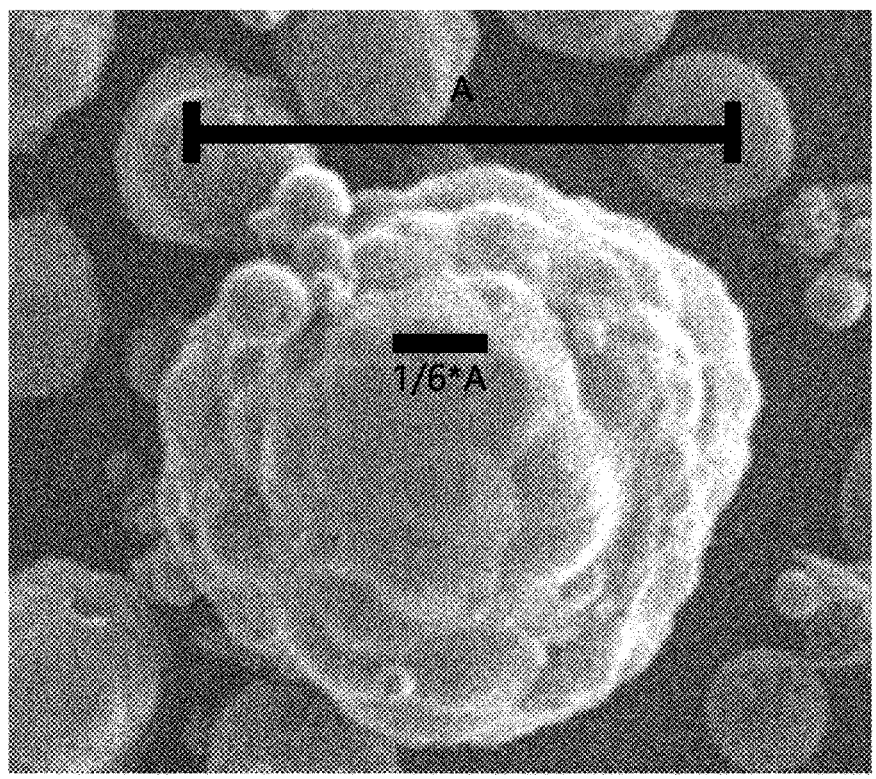
FIGS. 4 and 5 are views illustrating a structure of a biodegradable polymer microparticle for a filler of the present disclosure.
Figure 5:
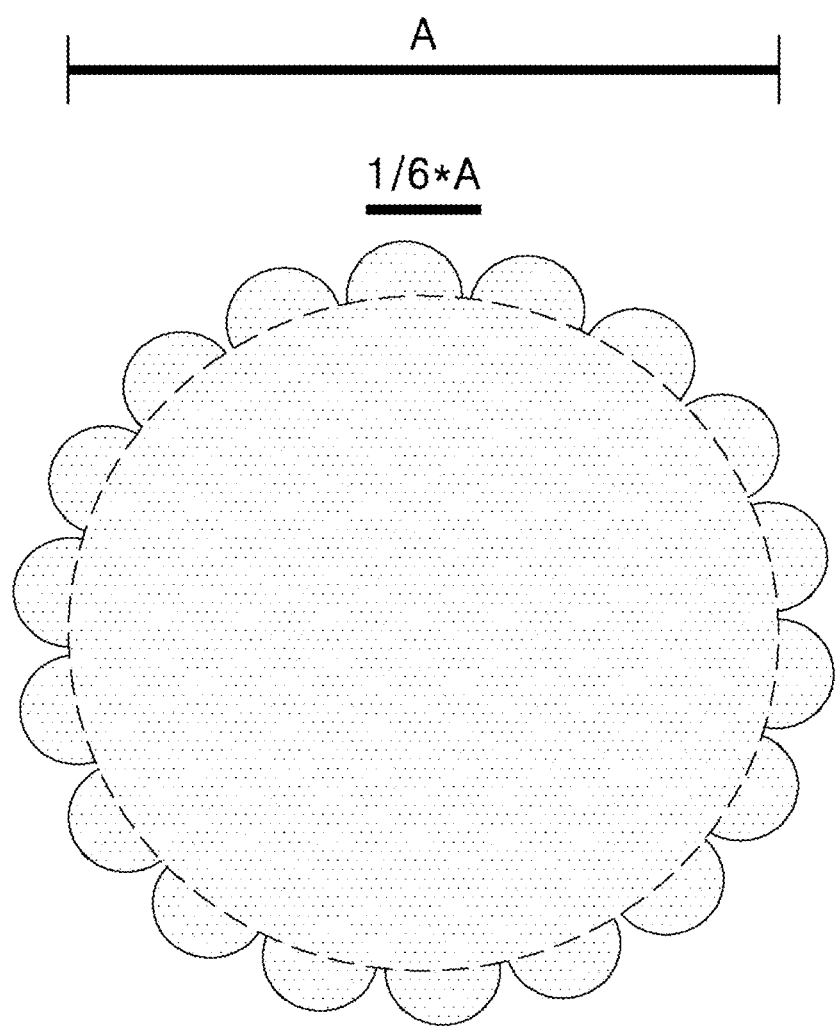

As illustrated in FIGS. 4 and 5, the raspberry-shaped biodegradable polymer microparticles for a filler had an average size of 150 μm, and in this evaluation example, it was assumed that the total size of the particle was 150 μm. Furthermore, the diameter of the protruding hemisphere was calculated to be 25 μm, which was ⅙ of the total diameter, and a difference in surface area compared to a sample A which is a spherical microparticle having a smooth surface of a similar size is shown in Table 1.

Through the calculation of the following Table 1, it was confirmed that the surface area of the raspberry-shaped microparticles was twice the surface area of the spherical microparticle having the smooth surface.

TABLE 1

|  | Sample A | Sample C (Example 1) |
|---|---|---|
| Surface area (cm$^2$) | 7.07143 * 10$^{-4}$ | 1.414286 * 10$^{-3}$ |
| Surface area ratio | 1 | 2 |

Evaluation Example 4: Average Particle Diameter and Particle Distribution Characteristics The average particle diameter, $D_{10}$, $D_{90}$, and particle distribution of the PDO particles manufactured according to the preparation example 1 were performed using a particle size analyzer (PSA).

In the following Table 3, span is represented by the following formula 1.

$$\text{Span} = (D_{90} - D_{10})/D_{50} \quad \text{[Formula 1]}$$

TABLE 2

| Division | $D_{50}$ | $D_{10}$ | $D_{90}$ | Span |
|---|---|---|---|---|
| Preparation example | 100 | 20 | 180 | 1.6 |
| Comparative preparation example 1 | 90 | 20 | 180 | 1.78 |
| Comparative preparation example 2 | 150 | 90 | 250 | 1.07 |

Referring to Table 2, it was confirmed that the biodegradable polymer microparticles for a filler obtained according to the preparation example 1 had particle distribution characteristics that were more uniform and narrower than those of the biodegradable polymer microparticles of the comparative preparation examples 1 and 2.

Evaluation Example 5

The injections of the examples 1 to 5 and the comparative examples 1 to 5 were respectively charged into syringes, and 200 μl of the injection was injected into a hair-less mouse. The size of the injected part was measured for four weeks, and a change in size was continuously measured at a cycle of a predetermined period, and the results are shown in Table 3.

TABLE 3

| Division | Volume(%) immediately after procedure | Volume(%) after one week | Volume(%) after four weeks |
|---|---|---|---|
| Example 1 | 100 | 90 | 100 |
| Example 2 | 100 | 100 | 110 |
| Example 3 | 100 | 95 | 105 |
| Example 4 | 100 | 90 | 100 |
| Example 5 | 100 | 90 | 100 |
| Comparative example 1 | 100 | 10 | 60 |
| Comparative example 2 | 100 | 50 | 85 |
| Comparative example 3 | 100 | 10 | 70 |
| Comparative example 4 | 100 | 10 | 80 |

As shown in Table 3, it was confirmed that the injections of the examples 1 to 5 were significantly reduced in initial volume compared to those of the comparative examples 1 to 4.

Evaluation Example 6: Comparative Experiment of Dissolution Speed of Freeze-Dried Body Three samples of the freeze-dried bodies of the example 6 and the comparative examples 5 to 8 were respectively dissolved in a 10 ml volume vial containing 2 ml of water through voltex equipment, and compared results in difference are shown in Table 4.

TABLE 4

| Division | Average dissolution time |
|---|---|
| Example 6 | 4.8 minutes |
| Example 7 | 4.5 minutes |
| Example 8 | 5 minutes |
| Comparative example 5 | 15 minutes |
| Comparative example 6 | 12.5 minutes |
| Comparative example 7 | 15 minutes |
| Comparative example 8 | 13 minutes |

As shown in Table 4, it was confirmed that the freeze-dried bodies of the examples 6 to 8 had improved dissolution speed compared to the comparative examples 5 to 8.

While the present disclosure has been described with reference to the accompanying drawings, it will be understood by those skilled in the art that the present disclosure can be practiced in other specific forms without changing the technical idea or essential features thereof. Therefore, it is to be understood that the embodiments described above are illustrative and not limiting in all respects.

The invention claimed is:

1. A biodegradable polymer microparticle group, comprising:
a first biodegradable polymer microparticle having a core and a shell; and
a second biodegradable polymer microparticle having a core and a shell,
wherein the cores of the first biodegradable polymer microparticle and the second biodegradable polymer microparticle contain secondary particles including aggregates of a plurality of primary particles,
wherein the shells of the first biodegradable polymer microparticle and the second biodegradable polymer microparticle have a raspberry shaped structure,
wherein the first biodegradable polymer microparticle and the second biodegradable polymer microparticle comprise polydioxanone, wherein the content concentration in the core of the first biodegradable polymer microparticle is higher than the content concentration in the shell of the first biodegradable polymer microparticle, and the difference in the content concentrations between the core and the shell of the first biodegradable polymer microparticle is 0.01 to 3% by weight, wherein the second biodegradable polymer microparticle has the same content concentration in the core and in the shell, wherein the content of the second biodegradable polymer microparticle (B) is 6 to 8% by weight based on the total weight of the first biodegradable polymer microparticle (A) and the second biodegradable polymer microparticle (B), and wherein the average particle diameter of the plurality of primary particles is 3 to 15 μm, the average particle diameter of the secondary particles is 80 to 150 μm, the cores of the first biodegradable polymer microparticle and the second biodegradable polymer microparticle are 60 to 95% by volume, and the shells of the first biodegradable polymer microparticle and the second biodegradable polymer microparticle are 5 to 40% by volume with respect to the total volume.

2. The biodegradable polymer microparticle group according to claim 1, wherein the polydioxanone has a weight average molecular weight of 50,000 to 200,000 Daltons.

3. The biodegradable polymer microparticle group according to claim 1, wherein the first biodegradable polymer microparticle and the second biodegradable polymer microparticle have a porosity of 2 to 85%.

4. A freeze-dried body, comprising: the biodegradable polymer microparticle group of claim 1; and a biocompatible carrier.

5. The freeze-dried body according to claim 4, wherein the biocompatible carrier is one or more selected from Alginic acid and salt thereof, hyaluronic acid and salt thereof, carboxymethyl cellulose and salt thereof, collagen, Gelatin, and Elastin.

6. An injectable composition, comprising: the biodegradable polymer microparticle group of claim 1; and one or more selected from injection water, sterilized water, and distilled water.

7. The injectable composition according to claim 6, further comprising: a biocompatible carrier,
wherein the mixing weight ratio of the biodegradable polymer microparticle group and the biocompatible carrier is 80:20 to 20:80.

8. A method for manufacturing the biodegradable polymer microparticle group of claim 1, the method comprising:
a first operation of mixing a first composition containing organic solvent miscible with water and biodegradable polymers and a second composition containing first surfactant and water, and preparing a third composition containing biodegradable polymer microparticle precursors for a filler and stirring them;
a second operation of adding and mixing a fourth composition containing the first composition containing the biodegradable polymers, second surfactant, and water to a product of the first operation, and stirring them to prepare a fifth composition containing biodegradable polymer microparticle group;
and a third operation of separating the biodegradable polymer microparticle group from the fifth composition, wherein in the second operation, the feed rate of the fourth composition is faster than the feed rate of the second composition of the first operation,
wherein the total content of the first surfactant and the second surfactant is 30 to 50 parts by weight with respect to 100 parts by weight of the total content of the biodegradable polymer microparticle group,
wherein the stirring speed of the second operation is slower than the stirring speed of the first operation,
wherein in the second operation, the content of the second surfactant is more than the content of the first surfactant in the first operation, and
wherein the content of the first surfactant in the first operation is 5 to 20 parts by weight with respect to 100 parts by weight of the total content of the biodegradable polymer microparticle group, and the content of the second surfactant in the second operation is 25 to 30 parts by weight with respect to 100 parts by weight of the total content of the biodegradable polymer microparticle group.

9. The method according to claim 8, wherein in the first operation, the second operation, and the third operation, the reaction temperature is 20 to 25° C., the stirring speed is 300 to 500 rpm, and the pH is controlled to be 4 to 6.

10. The method according to claim 8, wherein the first surfactant and the second surfactant are independently selected from polyvinyl alcohol, polyoxyethylene sorbitan and salt thereof, soy Lecithin, and monoglyceride.

11. A method for manufacturing the freeze-dried body according to claim 5, the method comprising:
a first operation of mixing a first composition containing organic solvent miscible with water and biodegradable polymers and a second composition containing first surfactant and water, and preparing a third composition containing biodegradable polymer microparticle precursors for a filler and stirring them;
a second operation of adding and mixing a fourth composition containing the first composition containing the biodegradable polymers, second surfactant, and water to a product of the first operation, and stirring them to prepare a fifth composition containing biodegradable polymer microparticle group;
a third operation of separating the biodegradable polymer microparticle group from the fifth composition,
wherein in the second operation, the feed rate of the fourth composition is faster than the feed rate of the second composition of the first operation,
wherein the total content of the first surfactant and the second surfactant is 30 to 50 parts by weight with respect to 100 parts by weight of the total content of the biodegradable polymer microparticle group,
wherein the stirring speed of the second operation is slower than the stirring speed of the first operation,
wherein in the second operation, the content of the second surfactant is more than the content of the first surfactant in the first operation, and
wherein the content of the first surfactant in the first operation is 5 to 20 parts by weight with respect to 100 parts by weight of the total content of the biodegradable polymer microparticle group, and the content of the second surfactant in the second operation is 25 to 30 parts by weight with respect to 100 parts by weight of the total content of the biodegradable polymer microparticle group; and
a fourth operation of preparing a sixth composition by mixing the biodegradable polymer microparticle group and a biocompatible carrier after the third operation, wherein the biocompatible carrier is one or more selected from Alginic acid and salt thereof, hyaluronic acid and salt thereof, carboxymethyl cellulose and salt thereof, collagen, Gelatin, and Elastin.

* * * * *